United States Patent

Fujimiya et al.

[11] Patent Number: 5,953,133
[45] Date of Patent: Sep. 14, 1999

[54] SCANNING APPARATUS

[75] Inventors: Hitoshi Fujimiya; Kenji Yamamoto; Toshiaki Ito; Hisanori Nasu, all of Yokohama, Japan

[73] Assignee: Hitachi Software Engineering Co., Ltd., Kanagawa-ken, Japan

[21] Appl. No.: 08/641,424

[22] Filed: May 1, 1996

[30] Foreign Application Priority Data

Oct. 2, 1995 [JP] Japan .................................. 7-278379

[51] Int. Cl.⁶ ........................... H04N 1/04; G01N 21/00; G01B 11/00; H01L 31/14
[52] U.S. Cl. .......................... 358/474; 358/475; 358/480; 358/482; 358/484; 250/552; 356/344; 356/359
[58] Field of Search .................................. 358/474, 482, 358/483, 514, 515, 518, 461, 464, 484, 487, 494, 475, 480; 356/344, 359; 250/552

[56] References Cited

U.S. PATENT DOCUMENTS

| | | | |
|---|---|---|---|
| 4,420,772 | 12/1983 | Jacobs ..................................... | 358/474 |
| 4,746,942 | 5/1988 | Moulin ....................................... | 354/5 |
| 4,833,332 | 5/1989 | Robertson, Jr. et al. ............ | 250/458.1 |
| 4,950,895 | 8/1990 | Reinfelter .............................. | 250/327.2 |
| 4,992,664 | 2/1991 | Shimura et al. ...................... | 250/327.2 |
| 5,109,297 | 4/1992 | Izumi ..................................... | 359/216 |
| 5,190,632 | 3/1993 | Fujimiya et al. ....................... | 204/299 |
| 5,213,673 | 5/1993 | Fujimiya et al. ....................... | 204/299 |
| 5,223,917 | 6/1993 | Richert .................................. | 356/407 |
| 5,242,567 | 9/1993 | Fujimiya et al. ....................... | 204/299 |
| 5,404,024 | 4/1995 | Namaki .................................. | 250/586 |
| 5,434,682 | 7/1995 | Imamura et al. ...................... | 358/474 |
| 5,534,709 | 7/1996 | Yoshimoto et al. ................... | 250/588 |

FOREIGN PATENT DOCUMENTS 457 526 A2  11/1991  European Pat. Off. .
459 278 A1  12/1991  European Pat. Off. .
WO88/04045  6/1988   WIPO .

OTHER PUBLICATIONS

R.D. Brown, "A Recursive Algorithm for Sequency–Ordered Fast Walsh Transforms", IEEE Transactions on Computers, vol. C–26, No. 8, Aug. 1977, pp. 819–822.

Primary Examiner—Kim Yen Vu
Assistant Examiner—Mark Wallerson
Attorney, Agent, or Firm—Fay, Sharpe, Beall, Fagan, Minnich & McKee

[57] ABSTRACT

A scanning apparatus for scanning and reading a luminescent pattern of a sample in a flat-plate shape, having a placing member for placing the sample as an object for reading; a light condensing member for condensing light emitted from the luminescent pattern of the sample; a movement member for moving the light condensing member relative to the placing member; a light receiving member for dividing the light of the luminescent pattern of the sample condensed by the light condensing member into predetermined segments and receiving the light by scanning the light from the segments in a one-dimensional way; a photoelectrical conversion member for converting optical signals of the light received by the light receiving member into electrical signals; a control member for controlling a scan by the light receiving member in accordance with the electrical signals from the photoelectrical conversion member; and a data processing member for converting the electrical signals from the photoelectrical conversion member into digital signals and reconfiguring an image from the optical signals of the light from the segment received selectively in a one-dimensional way. The scanning apparatus can likewise scan and read a non-luminous or less luminous pattern of a sample by allowing light from a plane light source to transmit through the pattern of the sample.

4 Claims, 9 Drawing Sheets

PIXELS IN CARRIAGE DIRECTION

SCANNING APPARATUS

BACKGROUND OF THE INVENTION

The present invention relates to a scanning apparatus capable of scanning and reading a faint intensity of light emitted from a pattern of a sample of flat-plate shape at a high degree of sensitivity and, more particularly, to a scanning apparatus for scanning and reading, as image data, a pattern of luminescence emitted to a faint extent from a sample of flat-plate shape.

Techniques of analysis by gel electrophoresis have hitherto been extensively employed for fractionalization or analysis of structures of proteins or nucleic acids of high molecular substances of a living body. In many cases, however, the samples are to be obtained only in very small amounts by means of gel electrophoresis so that a secure and high degree of sensitivity to detection is particularly required for analysis of such samples.

Therefore, there have hitherto been applied techniques to a sample available in a very small amount, which involve labelling the sample as an object for analysis with a radioactive substance, pouring the labelled sample into a gel, subjecting the gel to electrophoresis, attaching the electrophoresed gel onto an X-ray film or the like for exposure to the sample labelled with the radioactive substance, transferring the light emitted from the radioactive substance to the X-ray film, and scanning and reading the light as an electrophoresis pattern of the sample.

It should be noted, however, that radioactive substances are very dangerous to handle and extreme care should be paid in handling and management of such radioactive substances. Therefore, recently, in order to require no use of such dangerous radioactive substances, there have been developed chemical luminescence methods which can detect an electrophoresis pattern of a sample at a high degree of sensitivity by means of chemical luminescence. Such chemical luminescence methods comprise labelling a sample with a substance such as an enzyme, admixing the sample with a luminescent substrate to cause a chemical luminescence due to a chemical reaction between the substance labelled in the sample and the luminescent substrate, and exposing the chemical luminescence emitted from the sample to a film to thereby provide a pattern of the sample.

More specifically, the results of blotting obtained by a chemical luminescence method are read by adding a luminescent substrate to a membrane to which a sample is attached, causing chemical luminescence from the sample in accordance with an amount of the sample, and exposing the chemical luminescence to a highly sensitive film, and scanning the chemical luminescence of the film. In some experiments, as chemical luminescence is very faint, a chemical luminescent substance capable of emitting chemical luminescence for a long period of time is required to be employed and a film having a high degree of sensitivity is also required to be employed. Even in such instances, ten to twenty hours are required for exposure of the sample to the highly sensitive film. After completion of the exposure, the film is then developed to provide a desired blotting image. In order to analyze the resulting image in a quantitative way, for example, it is further scanned with a scanner for general use in scanning documents and images, fetched in a personal computer, and analyzed by image processing.

In the above-described method using the highly sensitive film, a period of time to be set for exposure of a sample to the film has been determined, in many cases, by experiences and feelings of an operator on the basis of the amount of the sample used, the amount of a chemically luminescent substance to be used for the sample, temperature conditions and so on. Therefore, experimental results cannot be gained in a stable and secure manner and experiments have been forced to be carried out again in many cases. Further, such a conventional method is encountered with the problem that measurements cannot be done in a wide range due to the fact that a dynamic range should be determined by sensitivity characteristics of the film.

More recently, there has been made an attempt to solve the problems as described hereinabove, which is involved in reading the light of chemical luminescence directly as an image by means of a highly sensitive camera. In this case, in order to enable the camera to read a very small amount of the chemical luminescence, the sensitivity of the camera is required to be high enough to detect photons in a level of approximately $10^4$ per square centimeter per second. There are currently available two types of optical reading apparatuses that can achieve such a high degree of sensitivity; one being of such a type as amplifying optical signals with an image intensifier and then fetching an image, and the other being of such a type as improving a signal-to-noise ratio by controlling the generation of thermal noise by cooling a CCD image pick-up element.

The optical reading apparatus of the former type comprises the image intensifier of a structure in which a large number of capillaries for amplifying electrons, which are referred to as multi-channel plates, are interposed between photoelectric surfaces and the optoelectrons generated at the front photoelectric surface are caused to amplify to $10^4$ to $10^5$ times and be returned to optical signals at the rear photoelectric surface to be relayed them to a camera. The optical reading apparatus of this type, however, presents the problems that the cost of the image intensifier is very expensive and that the resolution capability of an image is restricted by the number of the multi-channel plates.

On the other hand, the optical reading apparatus of the latter type comprises a CCD image pick-up element of cooling type. A camera of this optical reading apparatus can reduce thermal noises by cooling the CCD element to minus several tens Celsius, thereby raising a signal-to-noise ratio. The CCD element is subjected to electronic cooling and the heat generated is sucked out by a medium such as water or liquid nitrogen. The CCD image pick-up element of such highly sensitive type can detect illuminance of approximately $10^{-8}$ lx and pick up an image. Further, it can gain a higher sensitivity by accumulating the light for a long period of time. The optical reading apparatus of the cooling type, however, presents the problems that a pump instrument and so on are required for circulating the cooling medium, thereby making the apparatus bigger in size, and that costs for the apparatus itself and maintenance become expensive.

Further, the problem common in the optical reading apparatuses of camera type exists in the fact that the number of pixels of the image pick-up element is as small as 512 by 512, in usual cases, and as much as 1,024 by 1,024, in larger cases. When an image of a pattern of a sample is to be scanned and read by the image pick-up element having such a small number of pixels, however, distortion is likely to be introduced in the optical system, and enlarging or reducing of the pattern may be caused to occur so continuously and change so easily that accuracy in spatial reproduction of an image becomes lowered.

It is to be noted, however, that an optical reading apparatus of a line sensor system of contact type for use in an image scanner for general use is suitable for a reading system having a high degree of accuracy in dimension and resolution. For the optical reading apparatus of such a line sensor system, there is employed a CCD line sensor which, however, requires illuminance as high as approximately 500 to 1,000 lx on a surface to be read. Hence, for scanners for scanning and reading documents and images for general use, a reading surface is illuminated with a light source such as a fluorescent light or the like to provide a sufficiently high degree of illuminance.

In order for the optical reading apparatus of the line sensor system of contact type to read chemical luminescence as high as approximately $10^{-8}$ lx, however, the CCD line sensor is required to be cooled to very low temperatures or it requires an image intensifier, like the CCD image pick-up elements for the camera as described hereinabove. Thus, the optical reading apparatus presents the problems that an optical detector constituting a light receiving portion becomes expensive, the line sensor becomes large in size because it is incorporated into a carriage disposed to be movable in the reading surface, and circulation of a cooling medium is difficult when the optical reading apparatus is of the cooling type.

SUMMARY OF THE INVENTION

Therefore, it is an object of the present invention to provide a scanning apparatus for scanning and reading a pattern of a sample at high degrees of quantization and accuracy in dimension, at low costs and at a high degree of sensitivity.

It is another object of the present invention to provide a scanning apparatus for scanning and reading a pattern of a faint intensity of light emitted from a sample in a sheet form at a high degree of sensitivity.

In order to achieve the objects as described hereinabove, in a first feature, the present invention provides a scanning apparatus for scanning and reading a luminescent pattern of a sample in a flat-plate shape, which is characterized by comprising: placing means for placing the sample as an object for reading; light condensing means for condensing light emitted from the luminescent pattern of the sample; movement means for moving the light condensing means relative to the placing means; light receiving means for dividing the light of the luminescent pattern of the sample condensed by the light condensing means into predetermined segments and receiving the light by one-dimensionally scanning the light from the segment; photo-electrical conversion means for converting optical signals of the light received by the light receiving means into electrical signals; control means for controlling a scan by the light receiving means in accordance with the electrical signals from the photo-electrical conversion means; and data processing means for converting the electrical signals from the photoelectrical conversion means into digital signals and reconfiguring an image from the optical signals of the light received from the segments selectively in a one-dimensional way.

In a second feature, the present invention provides a scanning apparatus which is characterized in that the control means for controlling the scan by the light receiving means carries out plural scans on an identical scanning line in accordance with the electrical signals from the photoelectrical conversion means.

Further, in a third feature, the present invention provides a scanning apparatus which is characterized in that the placing means comprises a sample-placing table member for placing the sample as a reading object and a sample covering member for covering the sample. The sample covering member covers the sample placed on the sample-placing table member in an optically closed space in association with the sample-placing table member, when the sample covering member is closed and the sample is to be scanned and read.

In addition, in a fourth feature, the present invention provides a scanning apparatus which is characterized in that the light from the luminescent pattern of the sample as the reading object is phosphorescence or accelerated phosphorescence emitted from the sample transferred onto a membrane, or chemical luminescence from the luminescent pattern of the sample giving out light on account of a chemical transformation of the sample.

Furthermore, in a fifth feature, the present invention provides a scanning apparatus which is characterized in that the data processing means further comprises correction processing means for correcting a periodical variation in a luminescent intensity in accordance with the control over the scan by the control means.

In a sixth feature, the present invention provides a scanning apparatus which is characterized in that the light receiving means comprises a shutter element forming the predetermined segments and a light guide wherein the light of the pattern of the sample is divided into the predetermined segments by the controlling of the segments by the shutter element, and the light of plural segments out of the predetermined segments is allowed to pass therethrough selectively in a one-dimensional way and to be led by the light guide for receipt by the light receiving portion.

Further, in a seventh feature, the present invention provides a scanning apparatus which is characterized by: a plane light source for illuminating the pattern of the sample with light in a flat form when the sample is not luminescent; placing means for placing the sample as an object for reading; light condensing means for condensing light transmitted through the pattern of the sample from the plane light source; movement means for moving the light condensing means relative to the placing means; light receiving means for dividing the light from the pattern of the sample condensed by the light condensing means into predetermined segments and receiving the light by scanning the light from the segments in a one- dimensional way; photoelectrical conversion means for converting optical signals of the light received by the light receiving means into electrical signals; control means for controlling a scan by the light receiving means in accordance with the photoelectrical conversion means; and data processing means for converting the electrical signals from the photoelectrical conversion means into digital signals and reconfiguring an image from the optical signals of the light from the segment received selectively in a one-dimensional way.

In the scanning apparatus according to the present invention having the features as described hereinabove, when a pattern of a chemically luminescent sample in a flat plate shape as a reading object is to be scanned and read, it is placed on the placing means, and the moving means moves the placing means and the light condensing means relatively, thereby starting reading the pattern of the sample. As the reading of the pattern of the sample is started, the light condensing means condenses the luminescence generated from the pattern thereof, and the light receiving means divides the light of the pattern thereof condensed by the light condensing means into a predetermined number of segments and scans the light from the segments in a one-dimensional way. The optical signals received by the light receiving means are then converted into electrical signals by the photoelectrical conversion means and the control means for controlling the scan by the light receiving means in accordance with the electrical signals converted by the photoelectrical conversion means. Further, the data processing means converts the electrical signals from the photoelectrical conversion means into digital signals and reconfigures an image from the optical signals of the segments of the light received selectively in a one-dimensional way by the light receiving means.

In the controlling of the scan to be conducted by the light receiving means, the control means controls the scanning of an identical scanning line at plural times in accordance with the electrical signals from the photo-electrical conversion means. The plural scans on the same scanning line allow the light receiving means to receive the light from a luminescent pattern from a sample emitting a faint intensity of luminescence at a high degree of sensitivity. Further, as described hereinabove, the placing means comprises the placing table member for placing the sample as the reading object and the covering member for covering the sample, and the covering member covers the sample placed on the placing table member in an optically closed space, when the sample is read, whereby noise from outside light can be blocked and a pattern of a very faint chemical luminescence can be read at a high degree of sensitivity.

In the scanning apparatus according to the present invention, the light from the luminescent pattern of the sample to be scanned as the reading object is phosphorescence or accelerated phosphorescence emitted from the sample transcribed onto a membrane, or chemical luminescence from a luminescent pattern of a sample giving out light on account of a chemical transformation of the sample. Further, the data processing means contains a correction processing means for correcting a periodical variation of intensity of luminescence in accordance with the control of the scan by the control means. Therefore, the scanning apparatus can read the pattern of the sample, even if it may vary its luminous energy, like luminescence from a luminescent pattern of the sample by a chemical transformation, by correcting a variation in the luminous energy.

Further, the light receiving means has the shutter element forming the predetermined segments and the light guide. When it receives the light from the luminescent pattern of the sample, the light of the luminescent pattern thereof can be divided into the predetermined segments by controlling the segment shutter by the shutter element, thereby allowing the light of the plural segments out of the divided segments to selectively pass therethrough in a one-dimensional way and guiding the light by the light guide.

The scanning apparatus according to the present invention is provided with the plane light source to illuminate the pattern of the sample with light in the plane form. This flat or plane light source can provide the pattern of the flat sample with light when the sample does not give out light. As a result, the light transmitted through the pattern of the sample can be treated in substantially the same manner as a luminescent pattern, so that the scanning apparatus having a mechanism like the mechanism as described hereinabove can likewise scan and read the pattern of the light transmitted through the pattern of the sample.

As described hereinabove, the present invention can provide the scanning apparatus that can scan and read a faint intensity of luminescence from a luminescent pattern of a sample, such as chemical luminescence, and realize a one-dimensional sensor portion of a contact type having a high degree of sensitivity at low cost, thereby making it easy to handle and enabling a faint intensity of the luminescence from the luminescent pattern of the sample to be scanned and read. In this case, the scanning apparatus according to the present invention utilizes a method for controlling the scan by a segment shutter appropriate for use with a one-dimensional CCD sensor as a high-sensitive optical sensor, so that the present invention can provide the scanning apparatus for scanning and reading the faint intensity of the luminescence from the luminescent pattern of the sample at low costs. In addition, the scanning apparatus according to the present invention is provided with the correction means for correcting the periodical variation in chemical luminescence so that it can scan and read an entire area of the pattern of the sample at a high degree of sensitivity without undergoing influences due to the periodical variations in chemical luminescence, even when the luminescent pattern of the sample generated by chemical luminescence is to be scanned and read.

Other objects, features and advantages of the present invention will become apparent in the course of the description that follows, with reference to the accompanying drawings.

DETAILED DESCRIPTION OF THE PREFERRED EMBODIMENTS

The present invention will be described in more detail by way of examples with reference to the accompanying drawings.

Figure 1:
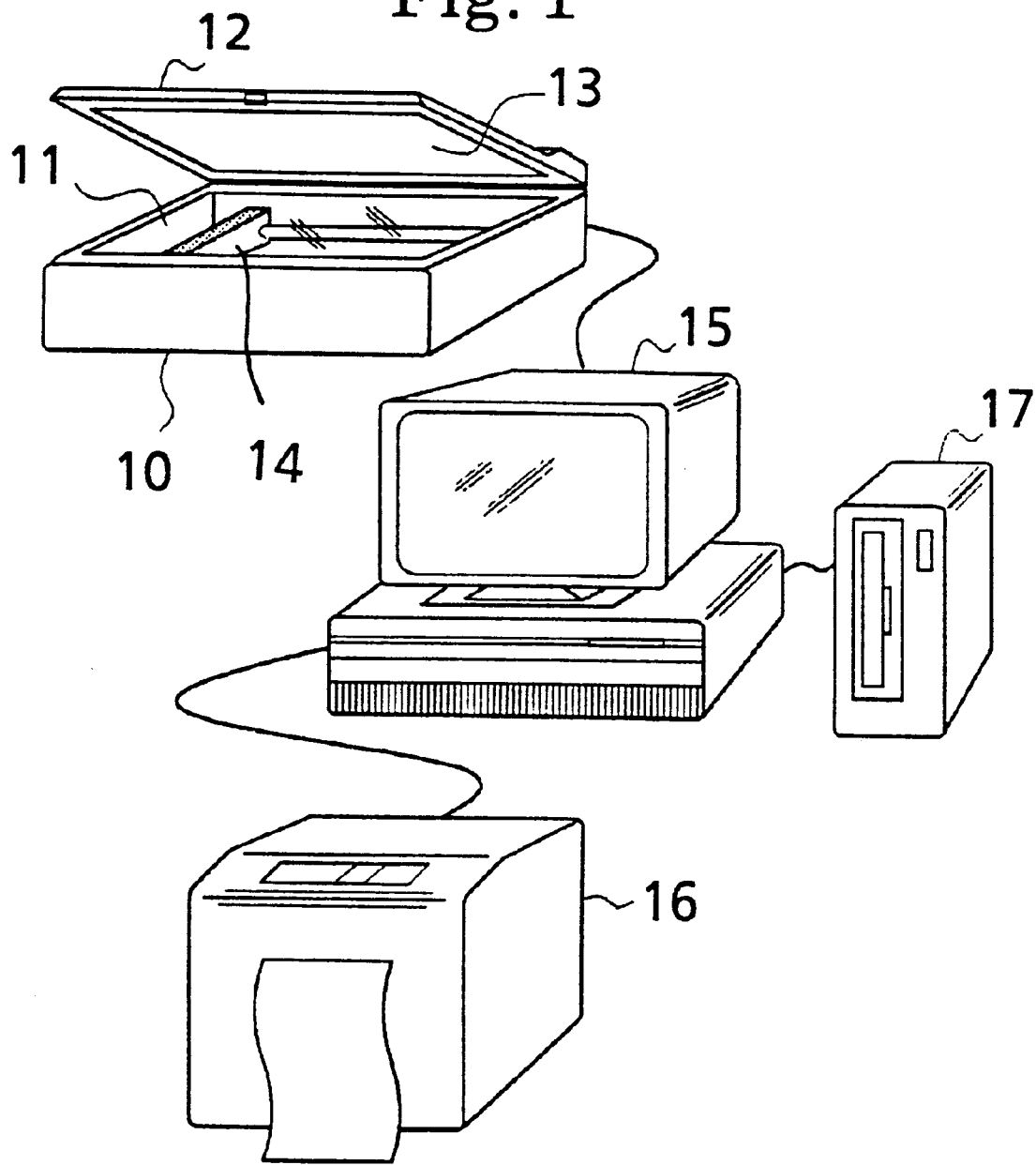
FIG. 1 is a block diagram showing an entire structure of a scanning apparatus according to an embodiment of the present invention.

FIG. 1 is a block diagram showing the entire structure of the scanning apparatus according to an embodiment of the present invention, in which reference numeral 10 denotes a main body of the scanning apparatus, reference numeral 11 a sample supporting table, reference numeral 12 a sample covering portion, reference numeral 13 a plane light source, reference numeral 14 a reading carriage having a light receiving portion, reference numeral 15 a data processing unit, reference numeral 16 a printer unit, and reference numeral 17 a data storage unit.

A description will be made of an outline of operations of the main body of the scanning apparatus in accordance with operations for reading luminescence emitted from a pattern of a sample with reference to FIG. 1. After the sample covering portion 12 of the main body 10 of the scanning apparatus is opened, a sample prepared previously is placed on the inside of the sample supporting portion 11 and the sample covering portion 12 is then closed. The sample supporting portion 11 is of box shape in which an upper portion of its outer peripheral side wall is provided with a groove at its central portion throughout its entire periphery, and the sample covering portion 12 is of lid shape in which a bottom side portion of its outer periphery is provided with a projection throughout its entire periphery. When the sample covering portion 12 is closed, it is so disposed as for its projection to be tightly engaged with the groove of the sample supporting portion 11 to form a closed room inside between the sample supporting portion 11 and the sample covering portion 12, thereby suppressing a leakage of light from the inside, because the intensity of luminescence of the luminous pattern of the sample is so very weak that a degree of sensitivity may be lessened if the light would leak from the inside.

The plane light source 13 is mounted on a rear surface of the sample covering portion 12, which faces a sample in a flat plate shape placed in the sample supporting portion 11, when the sample supporting portion 11 is a light source having a light emission surface in a plane shape to enable an illumination of the sample with light over the entire surface area of the pattern of the sample, when the sample giving out no light or only a lesser intensity of light is placed in the sample supporting portion 11. As a pattern of the light transmitted from the plane light source 13 through the pattern of the sample can be treated in substantially the same manner as a luminous pattern of the sample, the non-luminous pattern of the sample can be read as it is in substantially the same manner as reading the luminous pattern of the sample. As the reading sensitivity of the light receiving portion for reading the pattern of the sample is so high, the plane light source 13 can be applied to a sufficient extent even if a luminance of the plane light source 13 is not so high. As the plane light source 13, there may be employed, for example, an electroluminescence emitter (EL emitter) having a plane luminous surface.

As luminescence (fluorescence) from the luminous pattern of the sample usually can last for approximately ten and several minutes or longer, the reading carriage 14 having the light receiving portion is transferred in a predetermined direction, for example, in left and right directions as shown in FIG. 1, by a drive mechanism during a period of time during which the sample keeps giving out light, thereby allowing the light receiving portion to read the light from the luminous pattern in accordance with the reading position in which the reading carriage can read it. Although the structure of the light receiving portion of the reading carriage 14 will be described hereinafter, it is configured in such a way that the light emitted from the sample is condensed by a light condensing element such as a SELFOC lens array or the like, the light condensed is then divided into predetermined segments by a PLZT light shutter, the light of the size corresponding to the plural segments out of the reading segments of the sample is transmitted selectively in a one-dimensional way, the light is then led to the light guide to convert the optical signals and into electrical signals, the converted electrical signals are subjected to analog-digital conversion to and output.

The data of the digital signals of the luminous pattern of the sample read in the manner as described hereinabove is transmitted to the data processor 15 which in turn processes the transmitted data as image data, as needed, and re-configures an image of the luminous pattern, followed by displaying the resulting image on a display screen. The reconfigured data is stored in the data storage unit 17 as image data. The image data can be output by a printer unit 16. AS the printer unit 16, there may be employed preferably a printer printable at so-called multiple color "degrees", for example, a full color printer of a thermal sublimation type producing 256 different color degrees.

Figure 2:
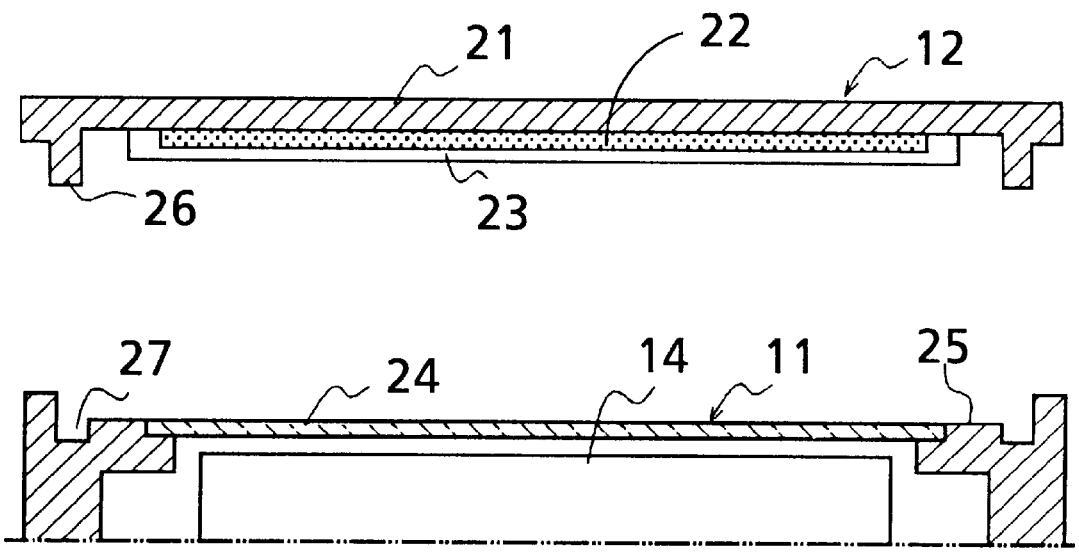
FIG. 2 is a sectional view showing an essential portion of a sample covering portion and a sample supporting table of a main body of the scanning apparatus according to the present invention.

FIG. 2 is a sectional view showing the essential portion of the sample covering portion and the sample supporting table of the main body of the scanning apparatus according to the present invention. As shown in FIG. 2, the sample covering portion 12 comprises a cover supporting member 21 for supporting a cover as a whole, a plane light emitter 22 and a protective sheet 23. On the other hand, the sample supporting portion 11 comprises a sample supporting plate 24 made of a transparent glass plate and a housing body 25 for supporting the sample supporting plate 24. In the inside of the housing body 25 is disposed the reading carriage 14 with the light receiving portion having the structure and the function as described hereinabove. The reading carriage 14 moves over a sample in a sheet form in forward and rearward directions by the drive mechanism (not shown).

As shown in FIG. 2, the cover supporting member 21 is provided at its outer peripheral side edge portion with a projection 26 extending downward, when the cover supporting member 21 is closed. On the other hand, the housing body 25 of the sample supporting portion 11 is provided at its outer peripheral side edge portion with a groove 27 that opens upward and tightly engages with the projection 26 when the sample supporting portion 11 is covered with and closed with the cover supporting member 21.

When the pattern of a sample to be scanned and read gives out light, the power source of the plane light emitter 22 is kept off. On the other hand, when the pattern of a sample is not luminous, the power source thereof is turned on and the plane light emitter 22 lights up after it has been confirmed that no luminescence given out from the sample has been detected by the light receiving portion for a predetermined period of time. Thereafter, the reading of the pattern of the sample is started. By the operations as described hereinabove, the scanning apparatus according to the present invention can scan and read the pattern of the samples, whether luminous or non-luminous, in substantially the same manner. It is to be noted herein that, when the pattern of the sample is not luminous, it is read by having the light receiving portion reading the light transmitted through the pattern thereof.

When a faint intensity of light from a portion of a sample is to start being read, the sample as a reading object is placed on the sample supporting plate 24 and the sample covering portion 12 is closed. As the sample covering portion 12 is closed, the sample is pressed downward by the protective sheet 23 mounted on the sample covering portion 12 and the projection 26 of the sample covering portion 12 is caused to engage with the groove 27 of the sample supporting portion 11 to provide an optically closed space between the sample supporting portion 11 and the sample covering portion 12 in which the sample is placed for reading, and the luminous pattern of the sample is read. The engagement of the sample covering portion 12 with the sample supporting portion 11 is made so tightly that no light is leaked into the inside of the optically closed space from the outside. The reading of the luminous pattern of the sample is started by an instruction from the data processor 15. Once the instruction to start reading is given, the reading carriage 14 starts moving in a predetermined direction and reads the luminous pattern of the sample. When the sample is in a film form and does not give out light, the power of the plane light emitter 22 is turned on and the plane light emitter 22 lights up, thereby allowing the light receiving portion to detect the light transmitted through the non-luminous pattern of the sample and to read the image by converting the optical signals into electrical signals.

Figure 3:
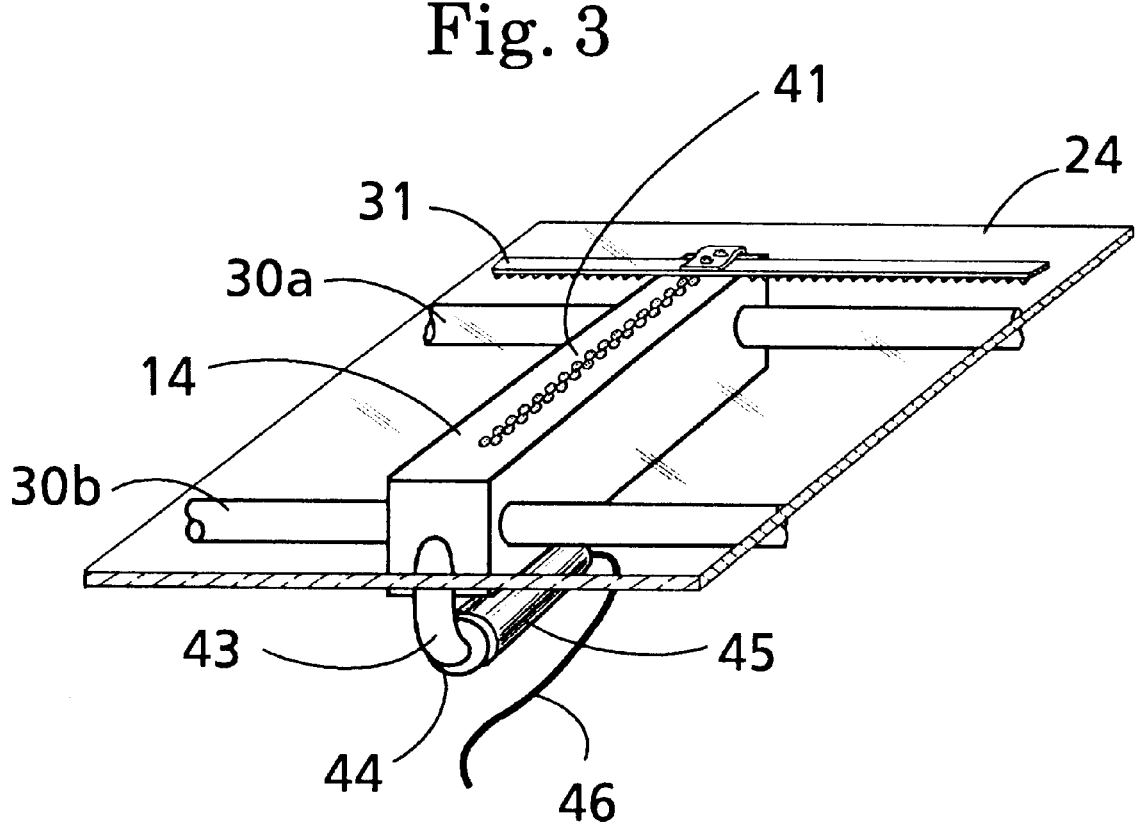
FIG. 3 is a perspective view showing a drive mechanism for a reading carriage of the main body of the scanning apparatus according to the present invention.
Figure 4:
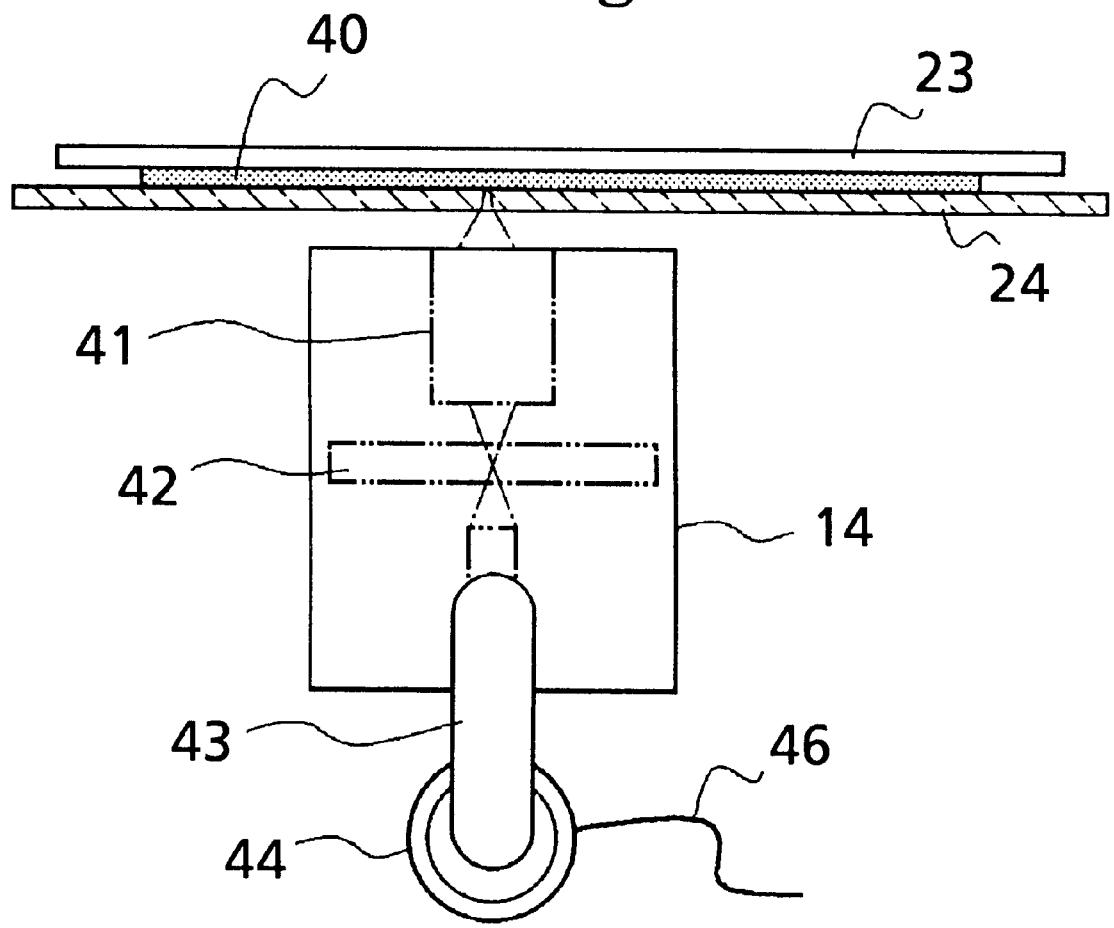
FIG. 4 is a side view showing a light receiving portion of the reading carriage of the main body of the scanning apparatus according to the present invention.
Figure 5:
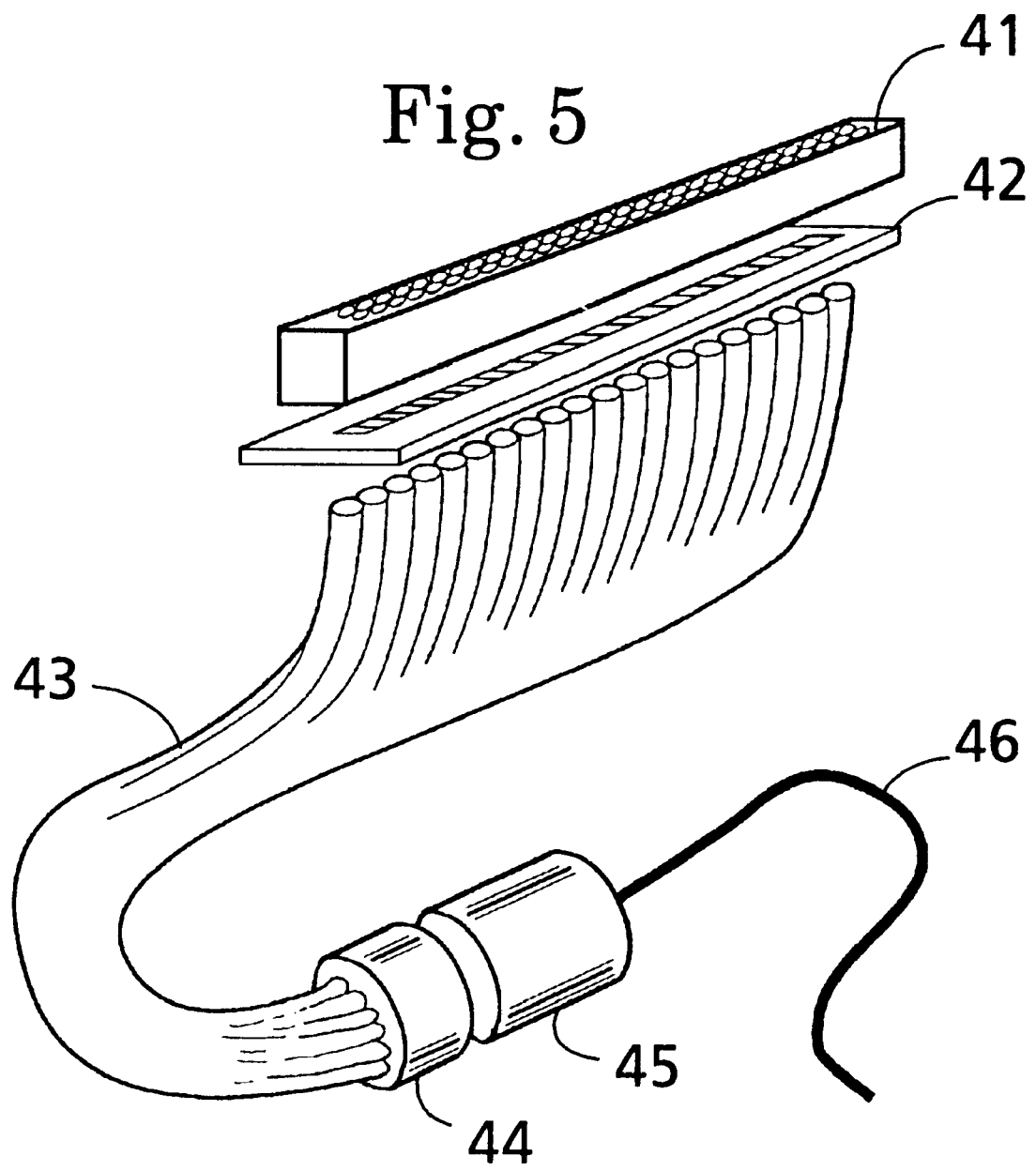
FIG. 5 is a perspective view showing the light receiving portion of the reading carriage of the main body of the scanning apparatus according to the present invention.

FIG. 3 is a perspective view showing the drive mechanism for the reading carriage of the main body of the scanning apparatus according to the present invention. FIG. 4 is a side view showing the light receiving portion of the reading carriage of the main body of the scanning apparatus according to the present invention. FIG. 5 is a perspective view showing the light receiving portion of the reading carriage of the main body of the scanning apparatus according to the present invention. As shown in FIGS. 3, 4 and 5, reference symbols 30a and 30b denote each a guide shaft, reference numeral 31 a timing belt, reference numeral 40 a sample in the form of a flat plate or a film, reference numeral 41 SELFOC lens array, reference numeral 42 a PLZT light shutter, reference numeral 43 a light guide, reference numeral 44 a cap for the light guide, reference numeral 45 a photo multiplier, and reference numeral 46 a wire for electrical signals.

As specifically shown in FIG. 3, the drive mechanism for the reading carriage comprises the reading carriage 14 disposed under the sample supporting plane 24 made of a transparent glass plate, and the reading carriage 14 in turn is provided with the light receiving portion comprising the SELFOC lens array 41, the light guide 43, the photo multiplier 45 and so on. The reading carriage 14 is held and guided by the guide shafts 30a and 30b to be slidable in left and right directions, as viewed in FIG. 3. The drive mechanism is structured in such a way that part of the timing belt 31 is fixed to the reading carriage 14 and the timing belt 31 in turn is connected to a stepping motor (not shown) for driving the reading carriage 14 to transmit the driving force of the stepping motor to the reading carriage 14. With this structure of the driving mechanism, the reading carriage 14 is moved in the predetermined direction by the rotation of the timing belt 31.

As specifically shown in FIG. 4, the light receiving portion of the reading carriage 14 comprises the SELFOC lens array 41, the PLZT light shutter 42, the light guide 43, the cap 44, and the photo multiplier 45, and it constitutes an optical system for reading the luminous pattern from the sample 40. The SELFOC lens array 41 comprises an optical part having the function as a condenser lens structured in such a manner that lenses having different refractive indexes are disposed on a rod with a lens disposed at a center of the rod having a refractive index varying from the refractive indexes of the lenses disposed at peripheral portions thereof. The lenses are disposed in the form of a one-dimensional array to form an accurate image of the luminous pattern of the sample in a one-dimensional way upon line on the focus on the opposite side.

The light from the luminous pattern emitted from the sample 40 is condensed by the SELFOC lens array 41 and the image is formed on the PLZT light shutter 42. The light passed through the segments of the PLZT light shutter 42 brought into the state in which the light can pass is transmitted to an inlet of the light guide 43 through which the light enters. The capability of a reading resolution is determined by the segments of the PLZT light shutter 42. In this example, there may be employed a one-dimensional PLZT light shutter having 16 pixels per mm.

A description will now be made of the process for controlling the PLZT light shutter in conducting a primary scan by the light shutter mechanism of the PLZT light shutter 42. In this example, a primary scanning line is divided into predetermined segments, the light is then allowed to pass one-dimensionally through the plural segments out of the reading segments of the sample, and the light passed is led by the light guide to a photoelectrical conversion element. By constituting the light receiving portion with the PLZT light shutter in the manner as described hereinbaove, a very faint intensity of light from the luminous pattern of the sample can be detected at a high degree of sensitivity.

Next, a description will be made of a specific way of the control to be made by the light shutter. With the scanning apparatus in accordance with the embodiment of the present invention, the primary scanning is made by the light shutter mechanism of a light shutter array using a piezoelectric material, e.g. ceramic PLZT, $(Pb, La)(Zr, Ti)O_3$. The switching time for the shutter operations of the light shutter array made of PLZT is 1 $\mu s$ or shorter and this switching time is very high in speed when compared with a liquid crystal shutter having the switching time of several $\mu s$. Therefore, if the shutter of the light shutter would be turned ON and then OFF one after another in the order of the arrangement of the cells for the reading segment out of the predetermined segments formed by the division of the scanning line of the pattern of the sample, only one cell is open at a certain moment. This lowers the efficiency and is not appropriate for measurement of light from the luminous pattern of the sample.

In order to improve this disadvantage, the scanning apparatus according to the present invention is configured in such a way that the measurement is made by bringing the plural cells in each segment always into ON states, thereby measuring the amount of the light received by each segment. Specifically, the measurement is conducted by changing combinations of the plural ON-state cells in each segment and, after the measurement has been finished, the results of the measurement for the combinations of the plural ON-state cells in each segment are subjected to an inverse operation on the basis of a control matrix of each cell to thereby provide the amount of the light received by each of the cells of the segment, i.e. the amount of the light emitted from the pattern of the sample.

In combining the plural ON-state cells, it may be possible to bring half of the cells in each segment as an object to be controlled by the shutter into an ON state at the same time. In this case, the amount of the light corresponding to the number of the simultaneous ON-state cells can be measured at one time so that a signal-to-noise ratio for the half of the cells can be improved simultaneously.

A more specific example of the control over the cells by the shutter will be described by taking a group of four cells as an object for controlling by the shutter. In order to apply the PLZT light shutter to this example, a scanning line to be scanned by the PLZT light shutter is divided into groups of four cells and each group is subjected to controlling by the PLZT light shutter.

More specifically, in this case, a matrix of orthogonal functions is employed in order to simplify the inverse operation for giving the amount of the light received by each cell. In the Hadamard matrix, "1" is set as "0" and "−1" is set as "off". When the former is indicated by reference symbol "0" and the latter is indicated by reference symbol "X", they can be shown as in Table 1 below. In Table 1 below, the amount of the light received by each cell, corresponding to each pixel, to be controlled by the shutter, is indicated by A, B, C and D.

TABLE 1

| Times of Measurement | A | B | C | D | Result of Measurement (Y) |
|---|---|---|---|---|---|
| 1 | O | O | O | O | Y1 |
| 2 | O | O | X | X | Y2 |
| 3 | O | X | O | X | Y3 |
| 4 | O | X | X | O | Y4 |

The measurement result Y of each measurement can be represented by Equation 1 as follows:

$$Y1 = A + B + C + D$$
$$Y2 = A + B$$
$$Y3 = A \phantom{+B} + C$$
$$Y4 = A \phantom{+B+C} + D$$

From the Equation 1 above, the amount of the light, ABCD, for each cell can be given by Equation 2 as follows:

$$A = (Y1+Y2+Y3+Y4)/2$$
$$B = (Y1+Y2-Y3-Y4)/2$$
$$C = (Y1-Y2+Y3-Y4)/2$$
$$D = (Y1-Y2-Y3+Y4)/2$$

As each of the measurement results Y1 to Y4, inclusive, contains a measurement error $\sigma^2$ having the same statistical properties, the error of each of the light A, B, C and D received by each cell is a bonding elementary probability density of the error of each of the measurement results Y1 to Y4, inclusive, so that the following relation can be given by Equation 3:

$$(\tfrac{1}{2})^2 4\sigma^2 = \sigma^2$$

When this relation is extended to n cells, the combined error can be given by Equation 4 as follows:

$$(1/(n/2))^2 n\sigma^2 = (4/n)\sigma^2$$

As is understood from the above equation, the error of the measurement result of the received light A, B, C and D of each cell is in reverse proportion to the number of cells, i.e. n cells. Hence, a signal-to-noise ratio can be improved in proportion to the number of the n cells. As the simple summation mean effect is in proportion to the square root of times when the same cell is measured repeatedly at plural times, the effects for improvement do not increase gradually. However, by using the control with the shutter by the matrix system of the matrix of the orthogonal functions as described hereinabove, remarkably greater effects for improvement can be gained, as compared with the simple summation mean effect, when the number of the cells exceeds 16.

Figure 6:
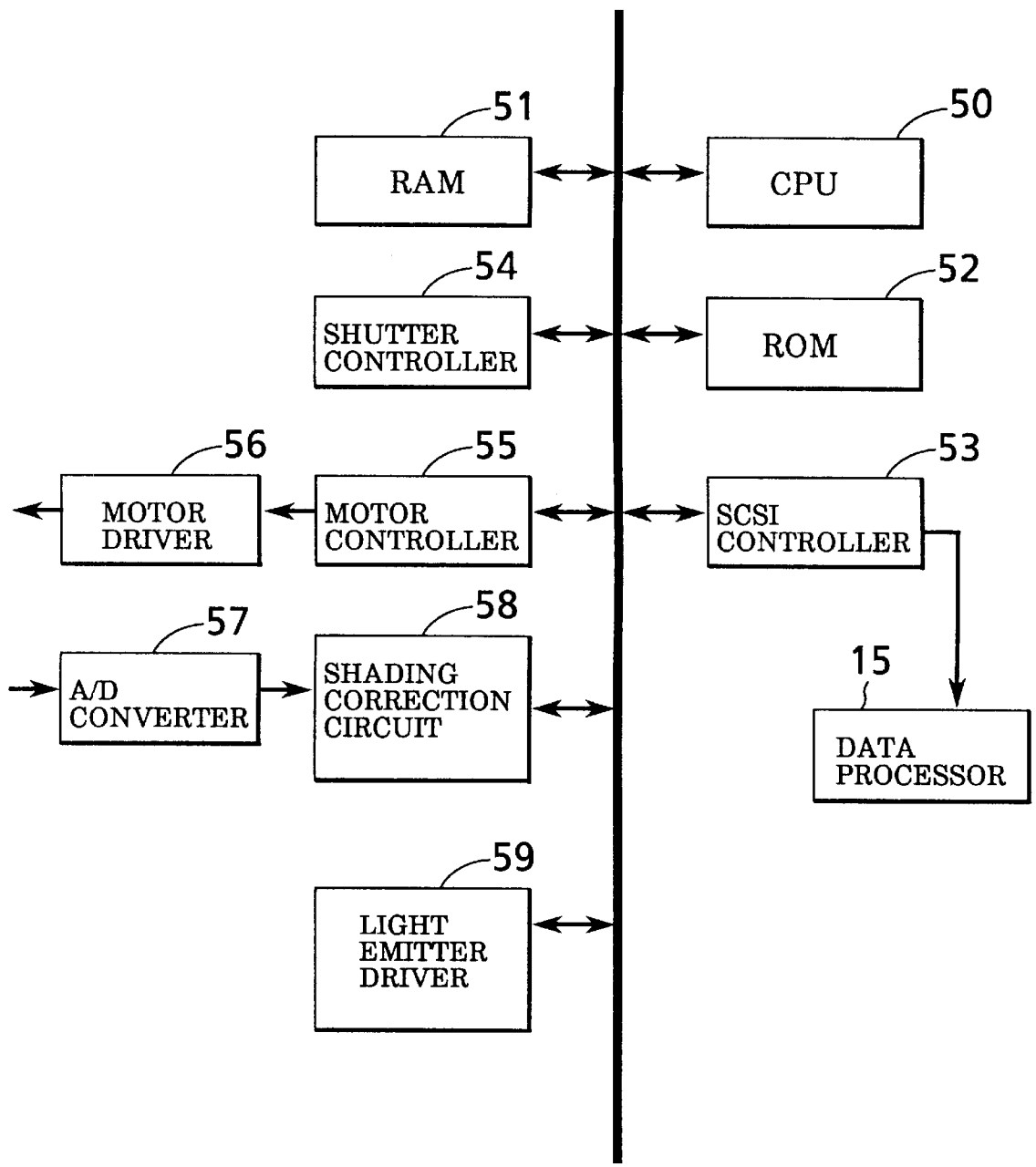
FIG. 6 is a block diagram showing a structure of an electrical line system of the main body of the scanning apparatus according to the present invention.

A specific way of the control by the shutter will be described. For example, when a sample pattern range of an A4 size is to be scanned and read at the density of 400 dpi, the total number of pixels in one line is 3,360 pixels so that it is difficult from the hardware point of view to fetch the data as large as the total number of pixels in a parallel manner at one operation. Hence, as the data bus width of a micro-processor (50; FIG. 6) for processing the control of the scanning apparatus is as wide as 32 bits, a shutter controller (54; FIG. 6) for controlling the light receiving portion is provided with a shift register corresponding to 3,360 pixels, and the control data for the shift register is entered while being shifted.

For the control pattern of the PLZT light shutter, the data of the control pattern for conducting the on/off control for the cells of each segment of the shutter has to be changed in each reading line. Accordingly, if the total data of the control pattern is to be rewritten whenever the reading lines are changed, the shift time for rewriting is wasted. Hence, in accordance with the present invention, the measurement is carried out by shifting the top row of the control matrix for conducting the on/off control of each cell of the PLZT light shutter by the portion corresponding to one line and by continuing the measurement to the next row of the matrix in substantially the same manner as described immediately hereinabove. Further, the reverse operations are conducted on the basis of the final results obtained by measuring four rows.

More specifically, the data of the first row of the control matrix of the control pattern of the PLZT light shutter is indicated as "OOOO" (where O is on), underlined below for ready reference only, and the measurement is carried out one after another, while shifting by four pixels as follows:

OOOOXXXXXXXXXXXXXXXX (Measurement result: Y11)

XXXXOOOOXXXXXXXXXXXX (Measurement result: Y12)

XXXXXXXXOOOOXXXXXXXX (Measurement result: Y13)

. . . . . . . . . . . . . . . . .

These measurement results (Y11, Y12, Y13, . . . ) are measurement values led to the light guide (43; FIG. 5) at each timing of measurement and received by the photo multiplier (45; FIG. 5).

The data of the second row of the control matrix is indicated as "OOXX" (where O is on and X is off), underlined below for ready reference only, and the measurement is carried out by shifting each cell of the PLZT light shutter by four pixels in substantially the same manner as described hereinabove.

OOXXXXXXXXXXXXXXXXXX (Measurement result: Y21)

XXXXOOXXXXXXXXXXXXXX (Measurement result: Y22)

XXXXXXXXOOXXXXXXXXXX (Measurement result: Y23)

. . . . . . . . . . . . . . . . .

The data of the third and fourth rows of the control matrix are indicated as "OXOX" (where O is on and X is off) and "OXXO". The measurement is carried out by shifting each cell of the PLZT light shutter by four pixels for each row in substantially the same manner as described hereinabove to give the measurement results (Y31, Y32, Y33, . . . ) and (Y41, Y42, Y43, . . . ) for the respective row. The rest of the rows are measured in substantially the same manner as described hereinabove.

As the measurement results are obtained by shifting each cell of the PLZT light shutter by four pixels, the light received for each cell is given in the same manner as the light is received by a single cell by subjecting the measurement results to the reverse operation as indicated by Equation 2. Further, based on the light received by each cell, the data of all the pixels is given in each pixel position of the pattern of the sample.

The description as made hereinabove is directed to the example where four pixels are treated as one unit for an object for controlling, the light received by each cell is measured, the reverse operation is conducted from the measurement results, and the data of the pixels is given. It should be noted herein, however, that the measurement can be made in substantially the same manner as described hereinabove by treating, for example, eight pixels or sixteen pixels as one unit. In such a case, the data length becomes longer so that the controlling can be made in substantially the same manner by lengthening the shift length of the shift register to adapt the longer data length.

In the method for the control over each cell by the shutter of the PLZT light shutter 42 in the light receiving portion of the scanning apparatus according to the present invention, even if the size of the control matrix is made larger or the number of rows to be measured is increased, the number to be shifted in the primary scanning direction is made larger at the same time so that the time required for one measurement becomes shorter relatively. As a result, by carrying out the shift processing at a sufficiently high speed, the measurement can be made without increasing the total time required for the measurement for the full pattern of the sample so much and at a high signal-to-noise ratio.

The light received by the control with the PLZT light shutter 42 is led through the light guide 43 to the photo multiplier 45 as a photoelectrical conversion element, as shown in FIG. 5. The light guide 43 comprises a bundle of optical fibers to detect a faint intensity of light from the pattern of the sample with high efficiency. More specifically, the light guide 43 to be preferably employed for the present invention is an optically molded part which has a number of optical fibers disposed on an array with their one side end portions bundled together. In this embodiment, as the optical fibers, there may be preferably employed plastic fibers each having a diameter of 0.25 mm to enable the receipt of a sufficient amount of the light from the PLZT light shutter.

In this embodiment, the light receiving portion can receive the light from the light guide 43 applied directly to the photo multiplier 45 through the cap 44. When the pattern of the sample is to be read after a particular wavelength has been removed, an interference filter or a colored glass filter may be interposed between the cap 44 and the photo multiplier 45. This structure enables multi-color scanning. Further, in this embodiment, the photo multiplier 45 is of a head-on type. However, it may be of a side-on type capable of complying with a distribution of wavelengths of the light emitted from the sample.

FIG. 6 is a block diagram showing the structure of the electrical system of the main body of the scanning apparatus according to the present invention. As shown in FIG. 6, the electrical system of the main body of the scanning apparatus comprises a microprocessor (CPU) 50 for implementing the controlling processing of the scanning apparatus, a read only memory (ROM) 52 for storing a controlling software, a random access memory (RAM) 51 for storing data temporarily or implementing other data processing, a shutter controller 54 for controlling the PLZT light shutter 42, a motor controller 55 for controlling a motor for controlling the driving of the reading carriage, a motor driver 56, an A/D converter 57 for subjecting electrical signals converted from optical signals received from the luminescent pattern of a sample to analog-digital conversion into digital signals, a shading correction circuit 58 for correcting a deviation peculiar to an optical measurement system including irregularities of intensity of the light received by the light receiving portion or a light source, a light emitter driver 59 for controlling the plane light emitter 22, a SCSI controller 53 for controlling an interface with an external data processing unit 15, and so on.

Figure 7:
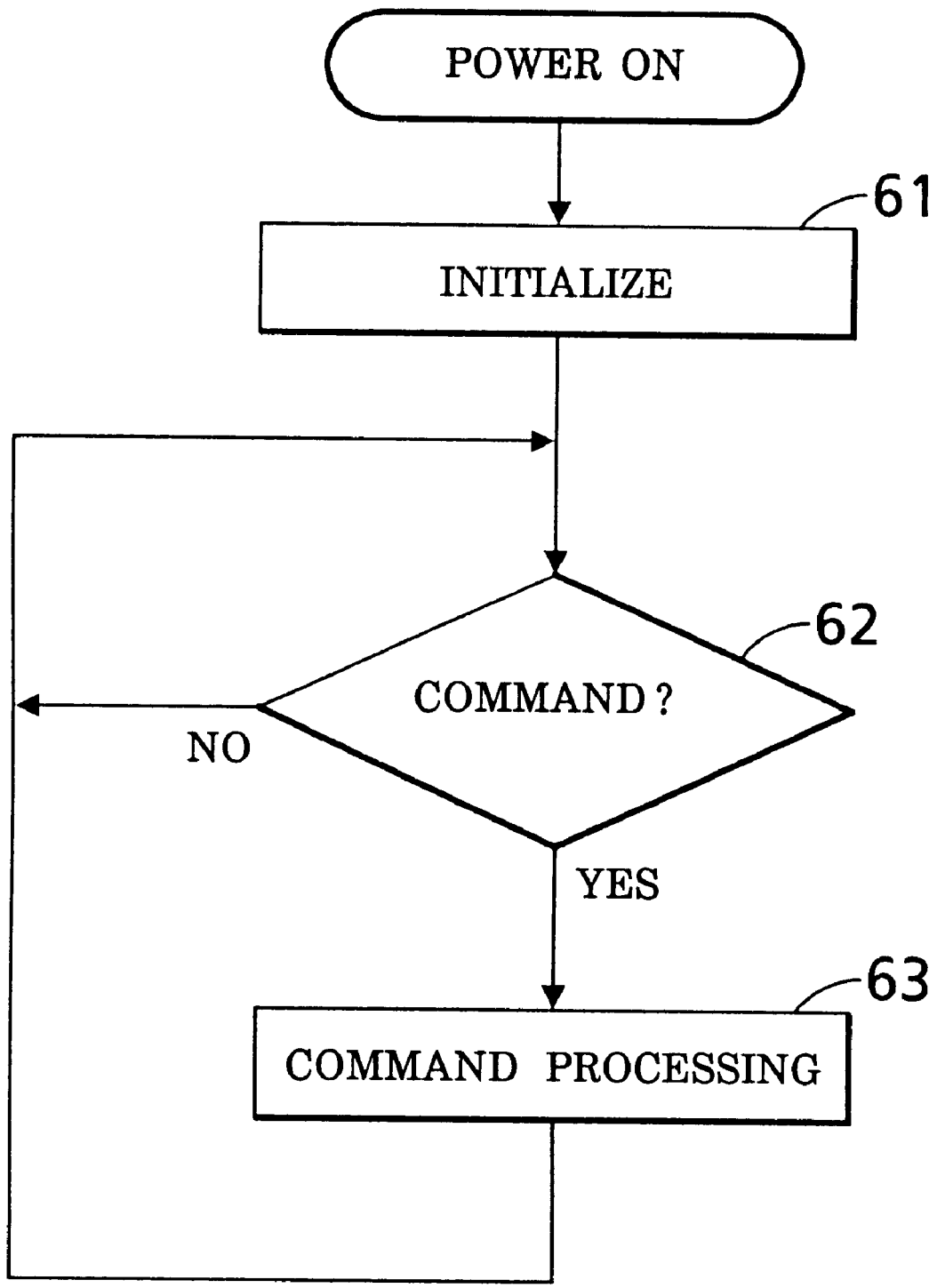
FIG. 7 is a flow chart showing an overall flow of operations of the electrical line system of the main body of the scanning apparatus according to the present invention.

FIG. 7 is a flow chart showing an overall flow of operations of the electrical system of the main body of the scanning apparatus according to the present invention. As shown in FIG. 7, the overall operations of the electrical system of the main body of the scanning apparatus start by turning the power on. When the power has been on, each portion of the apparatus is initialized at step 61. The initialization operation comprises checking out the read only memory (ROM) 52 and the random access memory (RAM) 51, checking out the operations of the power source and the light receiving portion by turning the power source on and off, initialization of an interface portion of the SCSI controller 53 for performing the controlling of the interface, checking out the operations of the drive system, alignment of the original point of the reading carriage, checking out the operations of the PLZT light shutter 42, reading of a pattern of irregularities of light from the plane light emitter 22, and so on.

After the initialization processing has been finished, the program goes to step 62 at which a command is waited for from the host side, i.e. data processor 15. When the command comes from the host side, the command is processed at step 63, followed by the return to step 62 at which a new command is waited for.

When the command is a command for reading, the operation is carried out by the light receiving portion to detect light from the sample for a predetermined period of time. If it is found as a result that the sample as a reading object does not give out light, on the one hand, a light emitter of the plane light source is turned on to illuminate the pattern of the sample with the light in a plane state in order to enable the reading of the pattern of the sample by means of the light transmitted through the pattern thereof. When the pattern of the sample is found to be luminous, on the other hand, the light receiving portion can detect the light from the luminescence from the sample so that the luminous pattern thereof can be scanned and read without keeping the plane light emitter 22 as the power source in an off state without turning the power on. Once the reading has been started, the control over the scan is made by conducting the primary and secondary scanning. While data on each one of the scanning lines is being obtained, it is subjected to shading correction processing by the shading correction circuit 58, followed by feeding to the data processor 15 through the interface of the SCSI controller 53. After the data on one line has been transmitted, the motor is driven to start reading the next line.

The operation for each line by the PLZT light shutter is carried out by controlling the shutter thereof in the way as described hereinabove. More specifically, a segment consisting of plural pixels is selected as one unit from the reference side of the start of scanning and the plural cells corresponding to the plural pixels for each unit are brought simultaneously into a light-transmittable state in accordance with the control matrix. Then, the amount of the light received by the light receiving portion is measured and the measured values are subjected to the reverse operation in accordance with the control matrix to give data on the value of the amount of the light of each pixel.

As described hereinabove, the scanning apparatus according to the present invention performs a primary scanning for each scanning line in such a state that the cells of the shutter of the PLZT light shutter corresponding to the plural pixels selected as one unit are brought into an ON state by the control by the shutter of the PLZT light shutter. Accordingly, a ratio in time of the plural pixels to the cells (duty ratio) in the light-transmitted state in each scanning line is so high that the light of the pattern of the sample can be read at a high degree of sensitivity. More specifically, the entire pixels of one line of the PLZT light shutter are grouped into segments each consisting of plural pixels and each of the segments is selected as one unit. Further, the ON/OFF control over each cell corresponding to each pixel is carried out by the shutter of the PLZT light shutter in accordance with the orthogonal functions and the reading is conducted while controlling approximately half of the pixels to be always brought into an ON state. Then, the value of the light amount at each pixel is given by subjecting the reading value to the reverse operation.

For example, when the "ON" state and the "OFF" state of the shutter cell for each pixel are represented as orthogonal functions [W] corresponding to "1" and "0", respectively, and the intensity of luminescence of the light in each segment on the sample is represented as the row vector [g], the measurement data [y] can be given as follows:

$$[y]=[W]\times[g]$$

Therefore, the row vector [g] can be obtained by taking the inverse matrix of [W] from the left side. As the orthogonal matrix, the matrix prepared by application of Walsh functions is appropriate. Further, for example, fast Walsh transforms (R. D. Brown: A Recursive Algorithm for Sequency-Ordered Fast Walsh Transforms; IEEE Transaction on computers, Vol. C-24, No. 8, August 1977, pp. 819–822 can also be applied because the "1,0" matrix and the appropriate scaling and offsetting.

The scanning apparatus according to the present invention requires approximately five minutes for reading the entire area of a reading region in a usual case. If the amount of the light emitted from the pattern of the sample decreases to a great extent during the reading period of time, the reading has to be conducted while performing the shading correction processing to make the degree of sensitivity average over the entire area thereof. In this case, the scanning apparatus according to the present invention is configured in such a fashion that, for example, the cells of the PLZT light shutter 42 for all the pixels are brought into an ON state before reading, the sum of the amounts of the light emitted in each scanning line is read for a short time, and the reference positions are set at several points by the instructions from the user.

Thereafter, the reading is started to read the amount of the light emitted from the entire area of a single scanning line at the nearest reference position for a predetermined period of time, for example, for 30 seconds or one minute. Then, the next area is read while correcting the decrement of the light emitted. When a new sample is to be scanned and read under substantially the same conditions as under the previously read conditions and the time required for a decrease of the amount of the light to be emitted from the new sample has already been known, the correction processing for the decrease in the luminous time of the sample can be conducted at the same time as the shading correction processing, by allowing the data processor 15 to feed correction data to the main body 10 of the scanning apparatus.

Figure 8:
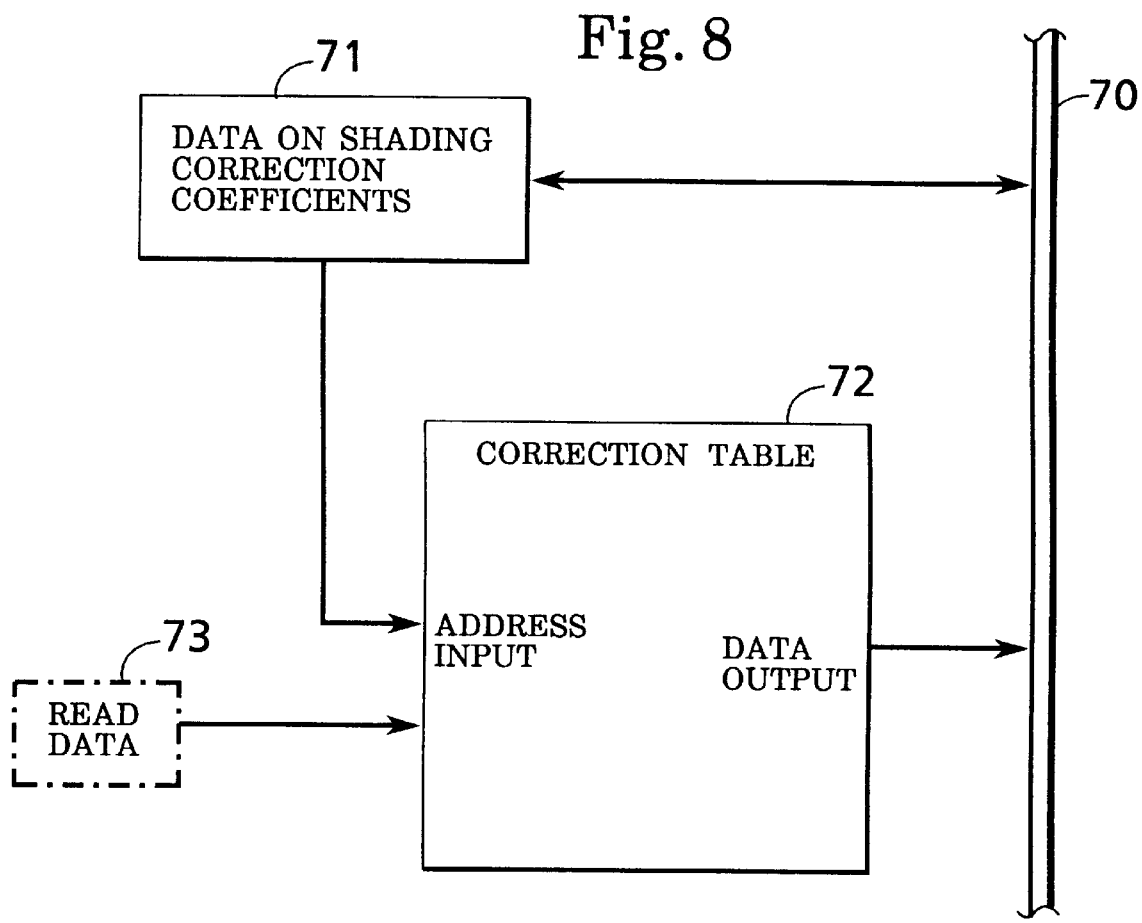
FIG. 8 is a block diagram showing a structure of an essential portion of a shading correction circuit.

FIG. 8 is a block diagram showing the structure of the essential portion of the shading correction circuit. In the shading correction circuit (58; FIG. 6), data including irregularities of sensitivity of the light guide 43 and the photo multiplier 45 in the reference area on the home position side is fetched and data on shading correction coefficients is set. For example, irregularities on the entire surface of the plane light emitter 22 are measured by moving the reading carriage 14 of the light receiving portion without placing any sample on the sample-placing table of the scanning apparatus, thereby providing the shading correction coefficients data and storing the measured data into writable non-volatile memory 71, as shown in FIG. 8. When the periodical decrease in the luminescence from the luminous pattern from the sample is known, the shading correction coefficients data to be stored in the non-volatile memory 71 may be multiplied with a correction coefficient to comply with the reading time in accordance with the direction in which the reading is to be conducted.

Figure 9:
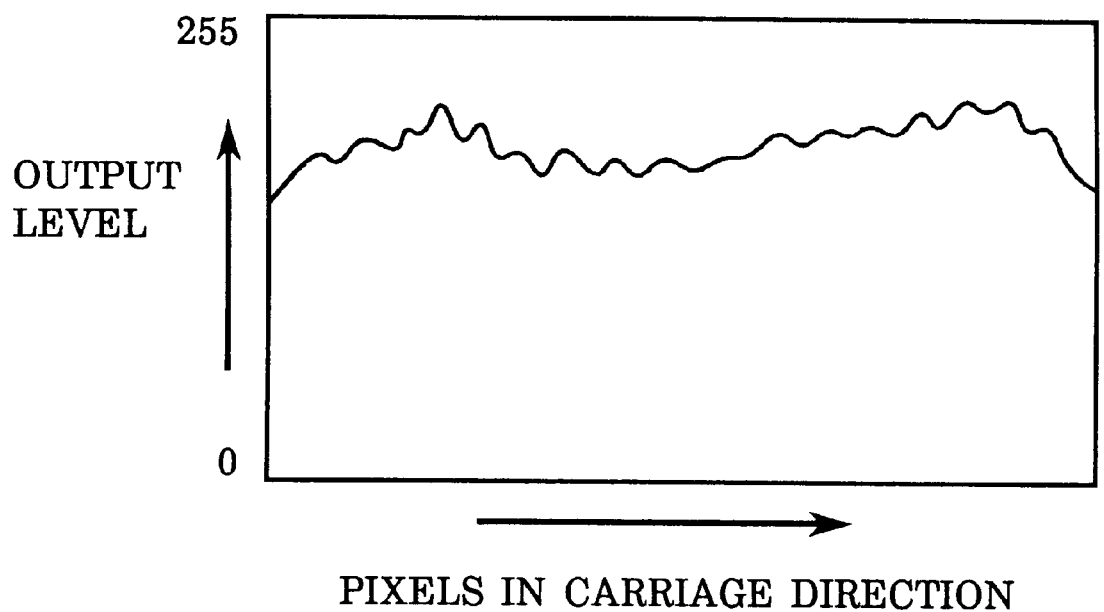
FIG. 9 is a graph showing a variation in output levels for reading with pixels in the carriage-direction.

When the pattern of the sample is read by setting the sample, the shading correction coefficients data is read out from the non-volatile memory 71 and signals of the amount of the light received from the luminous pattern of the sample read from the light receiving portion are subjected to analog-digital conversion (A/D conversion) to give reading data 73 which in turn is converted on the basis of a correction table 72 to provide final data. The correction table 72 for shading correction is provided because the conversion in association with the shading correction for reading the luminous pattern of the sample is to be made by a conversion system using a memory table. In the correction table 72, a value to be converted is written as data in advance in the memory table and the conversion in association with correction can be made by entering read data 73 on the data of the pixels after the A/D conversion as an address of the memory table and reading out the corrected data from the correction table 72, followed by the transmittance to the data bus 70. As a result, as shown in FIG. 9, the output level for reading can be corrected by the pixels in the carriage direction even if the output level would vary.

As the luminous pattern of the sample as the reading object to be scanned and read by the scanning apparatus according to the present invention, there may be mentioned, for example, chemiluminescence, luminescence from phosphorescence or accelerated fluorescence or electro-luminescence. When the sample is emitting accelerated fluorescence, it is coated on a substrate in the form of a very thin film so that it can be read as a pattern through which the light is transmitted from the plane light source. When the sample emits electroluminescence, the luminous pattern of the sample can be detected by allowing only the accelerated luminescence to be transmitted selectively by the optical filter disposed before the photo multiplier because kinds of wavelengths of the light source can be selected to some extent.

As described hereinabove, the scanning apparatus according to the present invention allows the light receiving portion of the reading carriage 14 to scan and read the pattern of a sample with a high degree of sensitivity by controlling the PLZT shutter. Hence, there can be employed the light source for the plane light emitter 22 which is sufficiently low in intensity of luminescence as compared with a light source (approximately 1,000 cd of a fluorescent lamp) employed for a scanner of the usual type. Therefore, a back light to be employed for a liquid crystal display or the like may also be employed for the plane light emitter 22 of the scanning apparatus according to the present invention. Further, there may be employed a combination of a fluorescent tube with a dispersion plate or an electroluminescence emitter. For the scanning apparatus in this embodiment of the present invention, there may also be employed an electro-luminescence emitter of approximately 50 cd.

It should be noted herein, however, that the scanning apparatus according to the present invention may be modified so as to implement the primary and secondary scan for reading a single pattern of the sample at plural times over the entire period of time during which the pattern of the sample keeps giving out light, in order to allow a very faint intensity of luminescence from the pattern thereof. In other words, the luminous pattern of the sample can be scanned and read by conducting the scanning operations for one pattern thereof at plural times.

For example, in an experiment referred to as genomic southern, nucleic acids extracted from the living tissues or the like are employed for the experiment as they are and the molecular numbers of the nucleic acids as samples for the experiment can be obtained in very small amounts. Hence, it is required to make the sensitivity of detecting each of the nucleic acids higher so as to satisfy the requirements by the experiment. For example, a light detector having the sensitivity of detection at $10^{-8}$ lx requires exposure to light for a period of time ranging from approximately thirty minutes to one hour. Further, as described hereinabove in connection with FIG. 3, the scanning apparatus according to the present invention has its reading carriage 14 containing the one-dimensional light receiving portion move mechanically, thereby carrying out the secondary scanning operation. However, if it takes a long time to move the reading carriage 14 for the secondary scanning operation, the amount of the light of the chemical luminescence may be decreased during the movement. In this case, there is the risk that irregularities in reading results occur over the entire area of the reading surface.

In order to compete with this problem, the scanning apparatus according to the present invention is configured in such a manner that the one secondary scanning operation for the luminous pattern of the sample can be conducted during a very short period of time that can neglect a periodical variation in the amount of the luminescence from the luminous pattern thereof. For example, the one secondary scanning operation is carried out in five minutes and the operations are repeated to scan the entire reading area of the luminous pattern of the sample. These operations can minimize adverse influences resulting from a periodical decrease of the amount of the luminescence from the luminous pattern of the sample. Further, the data read and obtained by every one of the secondary scanning operations is fed to the data processor 15 by which an image data from the cells corresponding to the pixels (i.e. an image data of each pixel obtained by the reverse operations) is subjected to integral processing and then displayed on a display screen. The integral processing can be conducted herein by subjecting the data to simple addition in a storage area and a display data to be displayed on the display screen in the data processor 15 may be an image data which is divided by the times of the scanning operations and subjected to average processing. This allows the user to readily confirm the status of the progress of reading operations and to proceed with the scanning operations without making errors that may often have occurred due to overexposure or the like when using a film.

In the scanning apparatus according to the present invention, the optical signals received are detected by the photo multiplier which in turn converts the optical signals into electrical signals. The electrical signals are then converted into digital signals by the A/D converter 57 and subjected to proceedings including shading correction processing, as shown in FIG. 6. When the pattern of the sample gives out light in a very faint intensity and the optical signals received are very low, the scanning apparatus can cause pulse-shaped signals corresponding to the incidence of photons from the photo multiplier to be amplified as they are and to convert into digital signals on the basis of the count value by the photon counting system. In the photon counting system, the pulse-shaped signals detected by the photo multiplier can be counted by setting the upper limit and the lower limit to the pulse signals to be counted, i.e. by conducting the filter operations at the signal level, in order to exclude small noise pulses caused to occur due to the emission of thermal electrons or very high pulses caused to occur due to radiation emission.

As described hereinabove, the scanning apparatus according to the present invention can read luminescence of the pattern of the sample with the reading carriage having the light receiving portion of a simple structure, even if the luminescence from the luminous pattern of the sample is of a very faint intensity like chemical luminescence, and further receive the light from the pattern of the sample with high efficiency in a like manner as a simple scanning system, thereby making the luminous pattern of the sample visible. Further, the scanning apparatus according to the present invention can read the pattern of the sample in a film form by using the plane light source (plane light emitter) like in a conventional manner, even if the pattern of the sample gives out little or no light. In addition, as the plane light source (plane light emitter) is not required to move mechanically in any direction, the apparatus in the shutter element can be made more compact in size and longer in system life than those of a reading type using a light source such as a fluorescent lamp, which is movable mechanically.

What is claimed is:

1. A scanning apparatus for scanning and reading a luminescent pattern of a sample in a flat-plate shape, comprising:

placing means for placing the sample as an object for reading;

light condensing means for condensing light emitted from the luminescent pattern of the sample;

movement means for moving said light condensing means relative to said placing means;

light receiving means for dividing the light emitted from the luminescent pattern of the sample and condensed by said light condensing means into predetermined segments, and for receiving the light from the segments simultaneously by one-dimensionally scanning the light from the segments;

photoelectric conversion means for converting optical signals of the light received by said light receiving means into electrical signals;

control means for controlling a scan by said light receiving means in accordance with the electrical signals from said photoelectric conversion means; and data processing means for converting the electrical signals from said photoelectric conversion means into digital signals, and for reconfiguring an image from the optical signals of the light from the segments received selectively by said one-dimensional scan;

wherein the data processing means reconfigures the image by converting light intensity values of the optical signals into image data by an inverse control matrix operation;

wherein the light receiving means includes a shutter having a plurality of light passing/blocking cells;

wherein each predetermined segment of divided light is received by a different group of said plurality of light passing/blocking cells, each group having more than one cell and thus defining one of said predetermined segments; and wherein said control means controls the scan by said light receiving means by selectively opening light passing/blocking cells in each group in accordance with the electrical signals from said photoelectric conversion means.

2. A scanning apparatus for scanning and reading a pattern of a sample in a thin flat-plate shape, comprising:

a plane light source for illuminating the pattern of the sample with light in a flat form when the sample is not luminescent;

placing means for placing the sample as an object for reading;

light condensing means for condensing light transmitted through the pattern of the sample from said plane light source;

movement means for moving the light condensing means relative to said placing means;

light receiving means for dividing the light from the pattern of the sample and condensed by said light condensing means into predetermined segments, and for receiving the light from the segments simultaneously by one-dimensionally scanning the light from the segments;

photoelectric conversion means for converting optical signals of the light received by said light receiving means into electrical signals;

control means for controlling a scan by said light receiving means in accordance with said photoelectric conversion means; and data processing means for converting the electrical signals from said photoelectric conversion means into digital signals, and for reconfiguring an image from the optical signals of the light from the segment received selectively by said one-dimensional scan;

wherein the data processing means reconfigures the image by converting light intensity values of the optical signals into image data by an inverse control matrix operation;

wherein the light receiving means includes a shutter having a plurality of light passing/blocking cells;

wherein each predetermined segment of divided light is received by a different group of said plurality of light passing/blocking cells, each group having more than one cell and thus defining one of said predetermined segments; and wherein said control means controls the scan by said light receiving means by selectively opening light passing/blocking cells in each group in accordance with the electrical signals from said photoelectric conversion means.

3. A scanning apparatus for scanning and reading a luminescent pattern of a sample in a flat-plate shape, comprising:

placing means for placing the sample as an object for reading;

light condensing means for condensing light emitted from the luminescent pattern of the sample;

movement means for moving said light condensing means relative to said placing means, light receiving means for dividing the light emitted from the luminescent pattern of the sample and condensed by said light condensing means into predetermined segments, and for receiving the light from the segments simultaneously by one-dimensionally scanning the light from the segments;

photoelectric conversion means for converting optical signals of the light received by said light receiving means into electrical signals;

control means for controlling a scan by said light receiving means in accordance with the electrical signals from said photoelectric conversion means; and data processing means for converting the electrical signals from said photoelectric conversion means into digital signals, and for reconfiguring an image from the optical signals of the light from the segments received selectively by said one-dimensional scan;

wherein the control means for controlling the scan by said light receiving means conducts plural scans of a scanning line for one luminescent pattern of the sample in accordance with the electrical signals from said photoelectric conversion means;

wherein the data processing means adds light intensity values of the optical signals for the plural scans, and divides the light intensity values by the number of scans, to reconfigure the image according to averaged optical signals of the light from the segments;

wherein the light receiving means includes a shutter having a plurality of light passing/blocking cells;

wherein each predetermined segment of divided light is received by a different group of said plurality of light passing/blocking cells, each group having more than one cell and thus defining one of said predetermined segments; and wherein said control means controls the scan by said light receiving means by selectively opening light passing/blocking cells in each group in accordance with the electrical signals from said photoelectric conversion means.

4. A scanning apparatus for scanning and reading a pattern of a sample in a thin flat-plate shape, comprising:

a plane light source for illuminating the pattern of the sample with light in a flat form when the sample is not luminescent;

placing means for placing the sample as an object for reading;

light condensing means for condensing light transmitted through the pattern of the sample from said plane light source;

movement means for moving the light condensing means relative to said placing means, light receiving means for dividing the light from the pattern of the sample and condensed by said light condensing means into predetermined segments, and for receiving the light from the segments simultaneously by one-dimensionally scanning the light from the segments;

photoelectric conversion means for converting optical signals of the light received by said light receiving means into electrical signals;

control means for controlling a scan by said light receiving means in accordance with said photoelectric conversion means; and data processing means for converting the electrical signals from said photoelectric conversion means into digital signals, and for reconfiguring an image from the optical signals of the light from the segment received selectively by said one-dimensional scan;

wherein said control means for controlling the scan by said light receiving means conducts the scan for a scanning line for one pattern of the sample at plural times in accordance with the electrical signals from said photoelectric conversion means;

wherein the data processing means adds light intensity values of the optical signals for the plural scans, and divides the light intensity values by the number of scans, to reconfigure the image according to averaged optical signals of the light from the segments;

wherein the light receiving means includes a shutter having a plurality of light passing/blocking cells;

wherein each predetermined segment of divided light is received by a different group of said plurality of light passing/blocking cells, each group having more than one cell and thus defining one of said predetermined segments; and wherein said control means controls the scan by said light receiving means by selectively opening light passing/blocking cells in each group in accordance with the electrical signals from said photoelectric conversion means.

* * * * *